United States Patent [19]

Tuller

[11] Patent Number: 5,071,626
[45] Date of Patent: Dec. 10, 1991

[54] OXYGEN SENSOR

[75] Inventor: Harry L. Tuller, Wellesley Hills, Mass.

[73] Assignee: Massachusetts Institute of Technology, Cambridge, Mass.

[21] Appl. No.: 318,894

[22] Filed: Mar. 3, 1989

[51] Int. Cl.$^5$ .................. G01N 31/12; G01N 27/00; H01C 7/00
[52] U.S. Cl. .................. 422/98; 422/94; 338/34; 73/23.31; 204/424
[58] Field of Search .................. 422/98, 94; 338/34; 73/23.32, 23.31; 436/137, 149; 204/424, 425

[56] References Cited

U.S. PATENT DOCUMENTS

| | | | |
|---|---|---|---|
| 4,314,996 | 2/1982 | Sekido et al. | 422/98 |
| 4,326,318 | 4/1982 | DeBruin et al. | 422/98 |
| 4,333,067 | 6/1982 | Kugimiya et al. | 338/34 |
| 4,505,803 | 3/1985 | Mase et al. | 422/98 |
| 4,507,643 | 3/1985 | Sunano et al. | 422/98 |
| 4,514,277 | 4/1985 | Sakurai et al. | 204/424 |
| 4,601,883 | 7/1986 | Sekido et al. | 422/94 |
| 4,677,414 | 6/1987 | Yates | 338/34 |
| 4,731,226 | 3/1988 | Takahata et al. | 338/34 |

OTHER PUBLICATIONS

Relva C. Buchanan, "Ceramic Materials for Electronics", Marcel Dekker, Inc., Chapter 5 (1986).
D. W. Johnson et al., "Fabrication of Ceramic Articles from High Tc Super-Conducting Oxides", Adv. Ceram. Mat. 2, pp. 364-371 (1987).
W. W. Davison et al., "High Tc Superconducting Films for Metallo-Organic Precursors", Mat. Res. Soc. Symp. Proc. on High-Temperature Superconductors, vol. 99, 1988, pp. 289-292.
M. Gurvitch and A. T. Fiory, "A Metal Allow Process for the Formation of Oxide Superconducting Films", in Mat. Res. Soc. Symp. Proc. on High-Temperature Superconductors, vol. 99, 1988, pp. 297-301.
P. H. Ballentine, Thin Films of Y-Ba-Ca-O by R. F. Sputtering, in Mat. Res. Soc. Symp. Proc. on High--Temperature Superconductors, vol. 99, 1988, pp. 335-338.
T. Wada et al., "Substitution Effect of Sr for Ba of High Tc Superconductivity $YBA_2CU_3O_{7-x}$ Ceramics", Jpn. J. Appl. Physics, Pt. 2, 26 [5]pp. L706-L708 (1987).
S. Ohshima et al., "Superconducting and Structural Properties of the New $Ba_{1-x}Ln_xCuO_{3-y}$ Compound System", Jpn. J. Appl. Physics, Pt. 2, 26 [5]pp. L815-L817 (1987).
G. S. Grader et al., "Oxygen Stoichimetry in $Ba_2YCu_3O_x$ and $Ba_2GdCu_3O_x$ Superconductors as a Function of Temperature", Adv. Cer. Mat. 2 [3B], pp. 649-655 (1987).
J. M. Tarascon et al., "3-d Metal Doping of the High Temperature Superconducti Perovskites La-Sr-Cu-O and Y-Ba-Cu-O" Phys. Rev. B36 [16] 8393 (1987).
S. Nagata et al., "High $T_c$ Thin Films of $(La_{1-x}M_x)yCuO_{4-\delta}$ (M=Sr, Ba, Ca) Prepared by Sputtering", Jpn. J. Appl. Physic., pt. 2, 26 [4], pp. L410-L412 (1981).
Y. Maeno et al., "Superconductivity in $YBa_2Cu_{3-y}Ni_yO_{7-\delta}$", Jpn. J. Appl. Physics, Pt. 2, 26 [5], pp. L774-L776.

Primary Examiner—Robert J. Warden
Assistant Examiner—Theresa A. Trembley
Attorney, Agent, or Firm—Choate, Hall & Stewart

[57] ABSTRACT

The sensor includes a sensing element of a copper oxide ceramic with perovskite related structurs. Electrical circuitry responsive to the conductivity of the sensing element is provided. This conductivity is a function of the gas partial pressure. A preferred ceramic oxide is in the Y-Ba-Cu-O system and these compounds exhibit a markedly greater dependence of conductivity on oxygen partial pressure than materials previously used.

17 Claims, 2 Drawing Sheets

OXYGEN SENSOR

The Government has rights in this invention pursuant to Grant Number DMR-84-18896 awarded by the National Science Foundation.

BACKGROUND OF THE INVENTION

This invention relates to oxygen gas sensors.

Oxygen gas sensors are utilized in such diverse areas as auto-exhaust sensors, sensors in combustion furnaces, steel and glass making, and combustible gas detectors. In the automobile application, oxygen gas sensors continuously monitor exhaust gas oxygen partial pressure which information is used in a feedback manner to adjust the fuel injection system. Known modulating resistive-type oxygen sensors exhibit an electrical conductivity dependence on $P_{O_2}$ given by the formula: $\sigma = \text{constant } P_{O_2}{}^{\pm 1/x}$ in which the factor x typically ranges between 4 and 6. Examples of known ceramics for such applications include $Co_{1-x}Mg_xO$ and $TiO_2$. This is a relatively weak dependence. Heretofore, high sensitivity of the oxygen sensor was not required, however, because oxygen partial pressure changed many orders of magnitude around the stoichiometric air fuel ratio operating point of conventional engines. In newly developed lean burn engines, however, the changes in oxygen partial pressure to be detected or controlled are small requiring more highly sensitive sensors.

SUMMARY OF THE INVENTION

The oxygen sensor according to the invention includes a sensing element of a copper oxide ceramic with perovskite related structures such as the Y-Ba-Cu-O system. A suitable ceramic oxide is $YBa_2Cu_3O_{7-x}$. Electrical circuitry is provided which is responsive to the conductivity of the sensing element. It is preferred that the ceramic oxide be thin and porous to insure rapid response. In one embodiment of the invention, the gas sensor includes apparatus to maintain the temperature of the sensing element constant so as to eliminate any temperature dependent effects.

In a preferred embodiment, the ceramic oxide sensing element resides on the surface of a hollow tubular substrate. The temperature regulating apparatus may be included within the hollow portion of the tubular substate.

The applicant herein has discovered that yttrium barium copper compounds exhibit a markedly greater dependence of conductivity on oxygen partial pressure than presently used materials. Thus, while commonly applied ceramic devices exhibit, at best, a proportionality between conductivity and oxygen partial pressure given by $\sigma = \text{constant } P_{O_2}{}^{\pm \frac{1}{4}}$, the material used in the present invention exhibits a relationship closer to $\sigma = \text{constant } P_{O_2}{}^{\frac{1}{2}}$. Thus, a two orders of magnitude change in $P_{OO_2}$ in the previous materials will result in a factor of 3.16 increase or decrease of $\sigma$, while with the materials of the invention, the same change will be reflected in a factor of 10 increase. This increase in sensitivity is crucial where changes in $P_{O_2}$ to be detected or controlled are small as in the newly developed lean burn engines.

Figure 1:
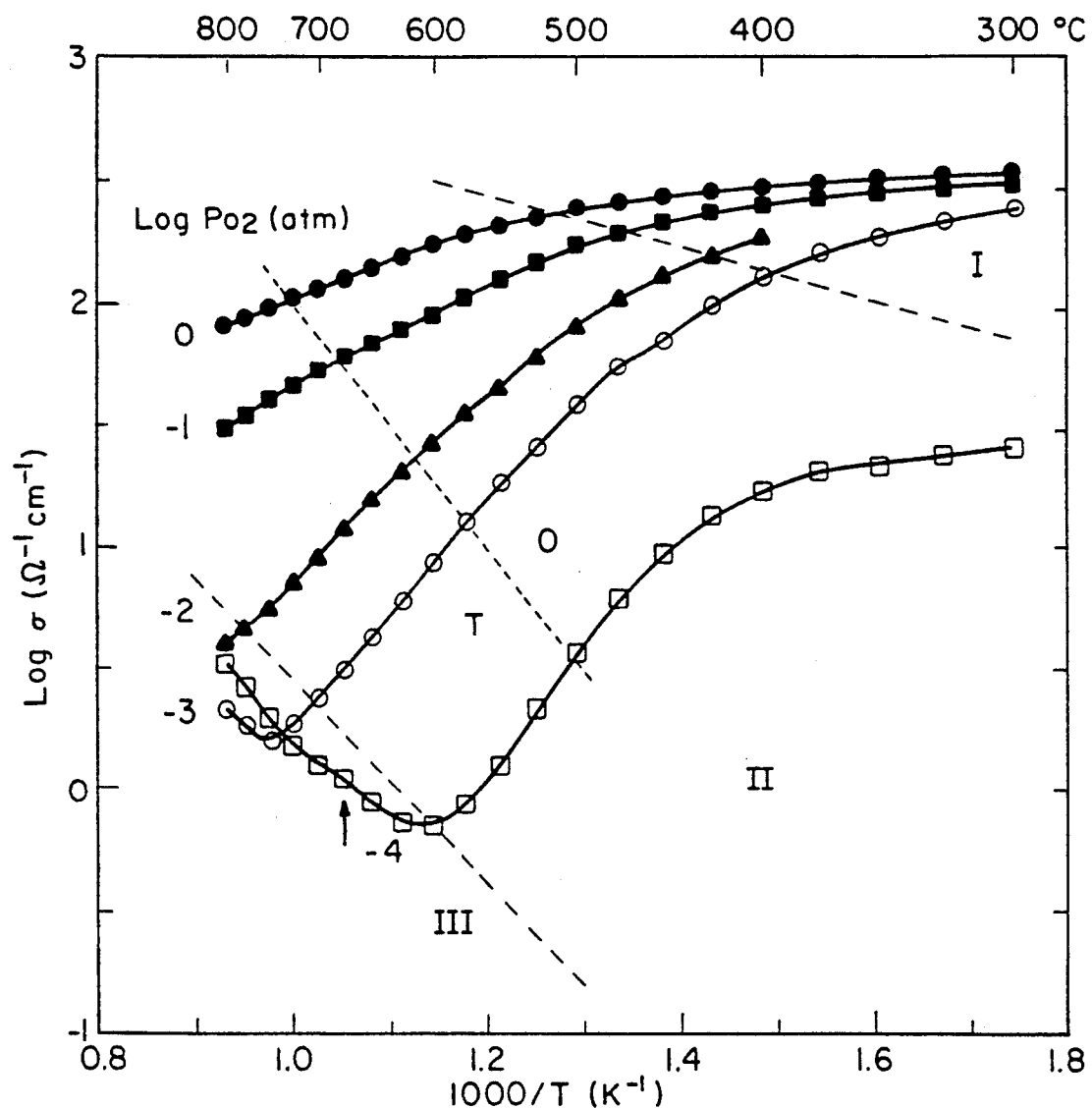
FIG. 1 is a graph of log conductivity versus reciprocal temperature at differing oxygen partial pressures.

DESCRIPTION OF THE PREFERRED EMBODIMENTS,

The present invention is based on the discovery by the applicant herein that yttrium barium copper oxide ceramics compounds exhibit a strong dependence of conductivity on oxygen partial pressure. In FIG. 1, a curve labelled 0 represents oxygen partial pressure at 1 atmosphere. Similarly, the curve labelled $-1$ represents an oxygen partial pressures of $10^{-1}$ atmosphere, and similarly for the curves marked $-2$, $-3$, and $-4$. Thus, at a selected operating temperature such as approximately 833° K. = 560° C. (1.2 on the reciprocal temperature scale), the curves are widely separated showing the high dependence of conductivity on oxygen partial pressure.

Figure 2:
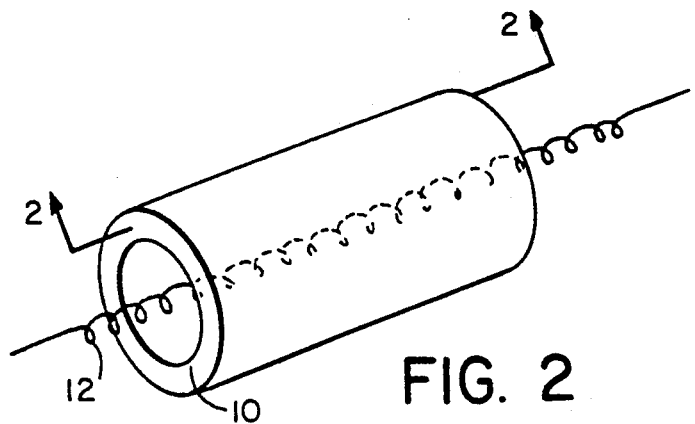
FIG. 2 is a schematic illustration of an oxygen sensor disclosed herein.

An oxygen sensor based on the characteristics displayed in FIG. 1 is shown in FIG. 2. A hollow tubular substrate 10 of a ceramic material such as $Al_2O_3$ includes a resistance heating element 12 residing in the open portion of the tubular substrate 10. The heating element 12 is operated by external circuitry (not shown) to maintain the temperature of the substrate 10 constant.

Figure 3:
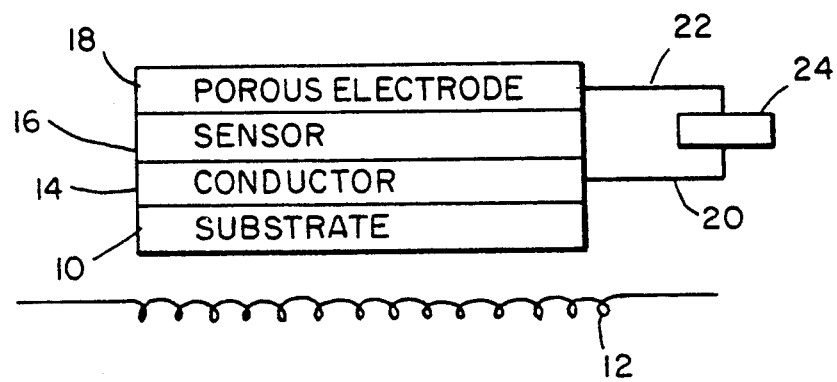
FIG. 3 is a cross-sectional view of the sensor of FIG. 2.

With reference now to FIG. 3, the outer surface of the substrate 10 includes a conductor 14 such as gold or platinum, sensor material 16 of Y-Ba-Cu-O or related compounds, and a porous electrode 18. Leads 20 and 22 connect the conductor 14 and the porous electrode 18 to an external circuit 24 which measures the conductivity of the sensor material 16. The electrode 18 is porous to permit oxygen to come into contact with the sensor 16. Furthermore, the sensor 16 should also be porous and thin to insure rapid response to oxygen partial pressure variations. A suitable thickness for the sensor material 16 is 0.1-250$\mu$ depending on the means of preparing the film.

Figure 4:
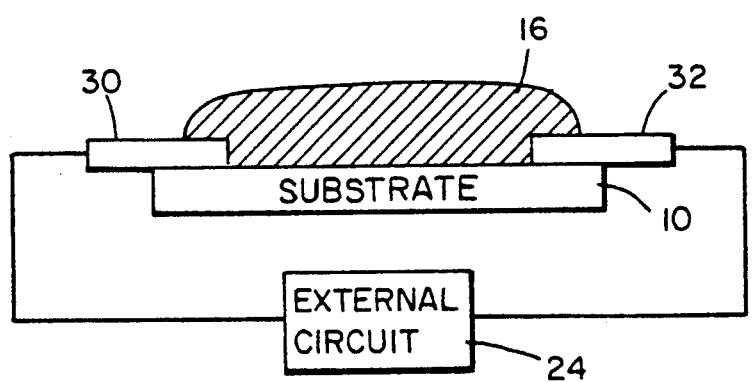
FIG. 4 is a cross-sectional view of a different arrangement of the sensor of FIG. 2.

Another embodiment of the invention is shown in FIG. 4. In this embodiment, the substrate 10 including electrical conductors 30 and 32 is coated with the sensing material 16. The conductors 30 and 32 are connected to the external circuit 24 which measures the conductivity of the sensing material 16. As with the embodiment of FIG. 3, the sensing material 16 should be thin and porous to insure rapid response to variations in oxygen partial pressure.

It is preferred that the sensing material 16 be $YBa_2Cu_3O_{7-x}$ or closely related materials. This material has recently been discovered to have high temperature superconducting characteristics and may be made according to the techniques disclosed in the literature concerning these materials. For example, see, *Fabrication of Ceramic Articles from High Tc Superconducting Oxides*, D. W. Johnson, et al., Adv. Ceram. Mat. 2, pp. 364-371 (1987); *High Tc Superconducting Films from Metallo-Organic Precursors*, W. W. Davison et al. in Mat. Res. Soc. Symp. Proc. on High Temperature Superconductors, Vol. 99, Eds. M. B. Brodsky, R. D. Dynes, K. Kitizawa and H. L. Tuller, 1988, pp. 289-292; *A Metal Alloy Process for the Formation of Oxide Superconducting Films*, M. Garvitch and A. T. Fiory, ibid. pp. 297-301; and *Thin Films of Y-Ba-Ca-O by R. F. Sputtering*, P. H. Ballentine et al., ibid. pp.

335-338, all of which are incorporated herein by reference.

A technique for making the sensors of the present invention is the citrate technique. According to this procedure, yttrium, barium, and copper metals are dissolved in citric acid and ethylene qlycol. This citrate polymer precursor may be applied to the substrate in thin layers by a spin-coating method. After the solution solidifies, the organic binder is removed by pyrolysis, leaving the ceramic oxide. Other techniques such as sputtering and vapor deposition may be used to deposit the sensor material 16 either on the conductor 14 in the embodiment of FIG. 3 or onto the substrate 10 in the embodiment of FIG. 4. It may be preferable to use such other techniques, if particularly thin films are desired. In any case, the desired level of porosity is controlled by the deposition conditions. For example, in films prepared by ceramic processing methods, some of the conditions which control porosity are particle morphology, sintering time and temperature, and sintering additives.

Other closely related materials which fall within the scope of this invention are generated by either partially or totally substituting other rare earths or other alkaline earths for the yttrium and the barium, respectively. For example, neodymium, europium, dysprosium, or holmium, etc. may be substituted for yttrium and calcium or strontium may be substituted for barium. It has been demonstrated that such substitutions result in materials possessing substantially similar properties to those of $YBa_2Cu_3O_{7-x}$. See, for example,

*Substitution Effect of Sr for Ba of High Tc Superconductivity $YBa_2Cu_3O_{7-x}$ Ceramics* by T. Wade et al., Jpn. J. Physics, Pt. 2, 26 [5] pp. L706-8 (1987).

*Superconducting and Structural Properties of the New $Ba_{1-x}Ln_xCuO_{3-y}$ Compound System* by S. Ohshima et al, ibid., pp. L815-17.

*Oxygen Stoichiometry in $Ba_2YCu_3O_x$, $Ba_2GdCu_3O_x$ and $Ba_2EuCu_3O_x$ Superconductors as a Function of Temperature* by G. S. Grader et al., Adv. Cer. Mat. 2 [3B], pp. 649-55 (1987).

*3d-Metal Doping of the High Temperature Superconducting Perovskites La-Sr-Cu-O and Y-Ba-Cu-O* by J. M. Tarascon et al., Phys. Rev. B36 [16] 8383 (1987).

*High Tc Thin Films of $(La_{1-x}M_x)CuO_{4-\delta}$(M=Sr, Ba, Ca) Prepared by Sputtering* by S. Nagata et al., Jpn. J. Appl. Physic., pt. 2, 26 [4], pp. L410-12 (1987).

all of which are incorporated herein by reference. In addition, other transition metals may be partially substituted for copper. For example, see

*Superconductivity in $YBa_2Cu_{3-y}Ni_yO_{7-\delta}$* by Y. Maeno et al., Jpn. J. Appl. Physics, Pt. 2, 26 [5], pp. L774-6.

also incorporated herein by reference.

It is recognized that modifications and variations will be apparent to those skilled in the art and it is intended that all such modifications and variations be included within the scope of the appended claims.

What is claimed is:

1. Gas sensor comprising:
   a sensing element comprising a copper oxide ceramic with perovskite related structures; and
   electrical circuitry responsive to the conductivity of the sensing element; the conductivity of the sensing element being a function of the gas partial pressure.

2. The sensor of claim 1 wherein the ceramic is porous.

3. The sensor of claim 1 wherein the ceramic is supported on the surface of a substrate.

4. The sensor of claim 3 wherein the substrate is a cylinder formed of a ceramic material.

5. The sensor of claim 1 further including temperature regulating apparatus to maintain the temperature of the sensing element substantially constant.

6. The sensor of claim 5 wherein the temperature regulating apparatus includes a resistance heater.

7. The sensor of claim 1 responsive to oxygen partial pressure wherein the ceramic oxide is $YBa_2Cu_3O_{7-x}$.

8. The sensor of claim 1 responsive to oxygen partial pressure wherein the ceramic oxide is in the R-E-Cu-O system, where R is selected from the group of rare earth elements and E is selected from the group of alkaline earth elements.

9. The sensor of claim 8 wherein R is yttrium.

10. The sensor of claim 8 wherein E is barium.

11. The sensor of claim 9 wherein E is barium.

12. The sensor of claim 8 wherein E is strontium.

13. The sensor of claim 9 wherein E is strontium.

14. The sensor of claim 8 wherein E is calcium.

15. The sensor of claim 9 wherein E is calcium.

16. Gas sensor comprising:
    a sensing element comprising a metal oxide ceramic comprising copper and at least one transition metal, said ceramic having perovskite related structure; and
    electrical circuitry responsive to the conductivity of the sensing element; the conductivity of the sensing element being a function of the gas partial pressure.

17. The sensor of claim 16 wherein said at least one transition metal includes nickel.

* * * * *

UNITED STATES PATENT AND TRADEMARK OFFICE
CERTIFICATE OF CORRECTION

PATENT NO. : 5,071,626　　　　　　　　　　　　　　Page 1 of 2
DATED : December 10, 1991
INVENTOR(S) : Harvey L. Tuller It is certified that error appears in the above-indentified patent and that said Letters Patent is hereby corrected as shown below:

Column 1, line 18: delete "$P_{O0.2}$" and insert therefor -- $P_{O2}$ --;

Column 1, line 19: delete "$P_{O0.2} \pm 1/x$" and insert therefor -- $P_{O2} \pm 1/x$ --;

Column 1, line 55: delete "$P_{O0.2} \pm 1/4$" and insert therefor -- $P_{O2} \pm 1/4$ --;

Column 1, line 57: delete "$P_{O0.2} \pm 1/2$" and insert therefor -- $P_{O2} \pm 1/2$ --;

Column 1, line 58: delete "$P_{O0.2}$" and insert therefor -- $P_{O2}$ --;

Column 1, line 62: delete "$P_{O0.2}$" and insert therefor -- $P_{O2}$ --;

Column 2, line 8: delete ",";

UNITED STATES PATENT AND TRADEMARK OFFICE
CERTIFICATE OF CORRECTION

PATENT NO. : 5,071,626
DATED : December 10, 1991
INVENTOR(S) : Harvey L. Tuller

It is certified that error appears in the above-indentified patent and that said Letters Patent is hereby corrected as shown below:

Column 3, line 6: delete "qlycol" and insert therefor -- glycol --;

Column 3, line 37: before "Physics" insert -- Appl. --;

Column 3, line 51: delete "$(La_1 - {}_xMx) Cu O_4 - \delta$" and insert therefor -- $(La_1 - {}_xMX)yCuO_4-\delta$ --; and Column 4, line 4: insert a space between "$\delta$" and "by".

Signed and Sealed this

Twenty-eighth Day of December, 1993

Attest:

BRUCE LEHMAN

*Attesting Officer*  *Commissioner of Patents and Trademarks*